United States Patent
Anderson et al.

(10) Patent No.: US 9,797,334 B2
(45) Date of Patent: Oct. 24, 2017

(54) TECHNIQUES FOR MITIGATING LOW-SPEED PRE-IGNITION CONDITIONS IN AN ENGINE AND A FUEL DELIVERY SYSTEM USING THE SAME

(71) Applicant: Southwest Research Institute, San Antonio, TX (US)

(72) Inventors: Garrett L. Anderson, Seguin, TX (US); Thomas E. Briggs, Jr., Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 15/006,489

(22) Filed: Jan. 26, 2016

(65) Prior Publication Data
US 2017/0211505 A1    Jul. 27, 2017

(51) Int. Cl.
| | | |
|---|---|---|
| *F02D 41/38* | (2006.01) | |
| *F02D 41/26* | (2006.01) | |
| *F02D 41/04* | (2006.01) | |
| *F02M 55/02* | (2006.01) | |
| *G01N 9/26* | (2006.01) | |

(52) U.S. Cl.
CPC ....... *F02D 41/3863* (2013.01); *F02D 41/045* (2013.01); *F02D 41/26* (2013.01); *F02M 55/025* (2013.01); *G01N 9/26* (2013.01); *F02D 2041/389* (2013.01)

(58) Field of Classification Search
CPC .... F02D 41/3863; F02D 41/045; F02D 41/26; F02D 2041/389; G01N 9/26; F02M 55/025

USPC .................................. 701/104, 111; 123/295
See application file for complete search history.

(56) References Cited

U.S. PATENT DOCUMENTS

| | | | | | |
|---|---|---|---|---|---|
| 2,023,568 | A | * | 12/1935 | Albersheim | G01F 1/50 73/861.63 |
| 3,293,320 | A | * | 12/1966 | Magearl | G01N 9/26 422/62 |
| 4,419,893 | A | * | 12/1983 | Baillie | G01N 9/26 73/439 |

(Continued)

FOREIGN PATENT DOCUMENTS

GB         1414797 A   *  11/1975   ............. E02F 3/907

OTHER PUBLICATIONS

RD 410036 A, Jun. 1998.*
<<http://www.swri.org/3pubs/brochure/d03/PPP-Consortium/PP-PConsortium.pdf>> downloaded Dec. 15, 2015.

*Primary Examiner* — Mahmoud Gimie
(74) *Attorney, Agent, or Firm* — Grossman, Tucker et al (57) ABSTRACT

Aspects and embodiments disclosed herein indicate a correlation exists between a specific gravity of combustible fuel and the occurrence of low-speed pre-ignition (LSPI) within engines. Thus techniques are disclosed herein for online measurement of the specific gravity of fuel within an engine, and allow for preventative measures to be executed to minimize or otherwise mitigate the incidence of LSPI when the calculated specific gravity of the fuel exceeds a predefined threshold. In an embodiment, the preventative measures may include, for example, altering or otherwise adjusting an engine map such that an injection timing scheme injects less poor-quality fuel into engine cylinders, thus advantageously preventing the engine from operating at full-power when conditions for LSPI are present.

22 Claims, 6 Drawing Sheets

(56) References Cited

U.S. PATENT DOCUMENTS

2011/0296911 A1* 12/2011 Moore .................... G01N 9/26
73/32 R

* cited by examiner

TECHNIQUES FOR MITIGATING LOW-SPEED PRE-IGNITION CONDITIONS IN AN ENGINE AND A FUEL DELIVERY SYSTEM USING THE SAME

FIELD

The present disclosure is generally directed to direct injection systems, and in particular, to a fuel delivery system configured to determine a specific gravity of fuel and adjust engine behavior to minimize or otherwise mitigate engine conditions giving rise to incidences of low-speed pre-ignition.

BACKGROUND

Internal combustion engines, such as gasoline engines, commonly employ a four-stroke working cycle. The four strokes may be referred to as the intake, compression, combustion (power), and exhaust strokes, which occur during two crankshaft rotations per working cycle of the engine. The working cycle may be understood to begin with the intake stroke with a piston at Top Dead Center (TDC) position, when the piston is closest to the cylinder head and farthest away from the axis of the crankshaft. A stroke may be understood to refer to a full travel of the piston from Top Dead Center (TDC) position to Bottom Dead Center (BDC) position, when the piston is furthest from the cylinder head and closest to the axis of the crankshaft.

During the intake stroke, the piston may be understood to descend from the top of a cylinder (e.g., TDC) to the bottom of the cylinder (e.g., BDC), reducing the pressure inside the cylinder. During the travel of the piston, an intake valve of the cylinder may open and a mixture of air and fuel may be introduced into the combustion chamber of the cylinder, under atmospheric or greater pressure, through an intake port. The intake valve may then close.

Thereafter, during the compression stroke, the piston may then return to the top of the cylinder, compressing the air-fuel mixture in the combustion chamber. Once the piston returns to TDC, the crankshaft will have undergone the first rotation of the working cycle. Next, the power stroke may be understood to begin when the piston is at TDC. After igniting the compressed air-fuel mixture with an igniter, such as a spark plug, the resulting pressure from the combustion of the compressed air-fuel mixture may then force the piston back down towards BDC. This stroke is the main source of the engine's torque and power.

The compressed air-fuel mixture within the combustion chamber may be ignited by the igniter near the end of the compression stroke. Igniting the air-fuel mixture before the piston reaches TDC may allow the resulting flame to better propagate and the mixture to more fully burn soon after the piston reaches TDC. However, if the ignition spark occurs at a position that is too advanced relative to piston position, the rapidly expanding air-fuel mixture may push against the piston as it is moving up during the compression stroke, causing possible engine damage. If the spark occurs too retarded relative to the piston position, maximum cylinder pressure may occur during the combustion stroke after the piston has traveled too far down the cylinder. This often results in lost power, high emissions, and unburned fuel.

After the combustion stroke, and during the exhaust stroke, the piston once again returns to TDC while an exhaust valve of the cylinder may be opened. This action may evacuate the products of combustion from the combustion chamber of the cylinder by pushing combustion products through an exhaust port. The exhaust valve may then close. Once the piston returns to TDC, the crank shaft will have undergone the second rotation of the working cycle and the engine will thereafter repeat the cycle.

In certain situations, the internal combustion engine may exhibit abnormal combustion. Abnormal combustion in a spark-initiated internal combustion engine may be understood as an uncontrolled deflagration occurring in the combustion chamber as a result of ignition of combustible elements therein by a source other than the igniter. One particular example of abnormal combustion may include pre-ignition. Pre-ignition may be understood as an abnormal form of combustion resulting from ignition of the air-fuel mixture prior to ignition by the igniter. Anytime the air-fuel mixture in the combustion chamber is ignited prior to ignition by the igniter, such may be understood as pre-ignition.

In some instances, pre-ignition occurs during high speed operation of an engine when a particular point within the combustion chamber of a cylinder may become hot enough to effectively function as a glow plug (e.g. overheated spark plug tip, overheated burr of metal) which can provide a source of ignition thus potentially causing the air-fuel mixture to ignite before ignition by the igniter. Such pre-ignition may be more commonly referred to as hot-spot pre-ignition, and may be inhibited by simply locating the hot spot and eliminating it.

More recently, vehicle manufacturers appear to have observed intermittent abnormal combustion in their production of turbocharged gasoline engines, particularly at low speeds and medium-to-high loads. More particularly, when operating the engine at speeds less than or equal to 2,000 rotations per minute (RPM) and under a load with a break mean effective pressure (BMEP) of greater than or equal to 10 bars, a condition which may be referred to as low-speed pre-ignition (LSPI) may occur in a very random or otherwise stochastic fashion. Unlike hot-spots that cause pre-ignition, LSPI is not necessarily tied to a particular location within an engine, and thus has raised numerous non-trivial challenges in the context of turbocharged gasoline engines.

SUMMARY

Aspects and embodiments disclosed herein identify a correlation exists between a specific gravity of combustible fuel and the occurrence of low-speed pre-ignition (LSPI) within engines. Thus systems and methods are disclosed herein for online measurement of the specific gravity of fuel within an engine, which may allow for preventative measures to be executed to minimize or otherwise mitigate the incidence of LSPI when the specific gravity of the fuel exceeds a predefined threshold. In an embodiment, the preventative measures may include, for example, altering or otherwise adjusting an engine map such that an injection timing scheme injects less poor-quality fuel into engine cylinders, thus advantageously preventing the engine from operating at full-power when conditions for LSPI are detected.

In an embodiment, a method for determining conditions giving rise to low-speed pre-ignition events in an engine is provided, with the method comprising receiving, by a controller, a first and second fuel pressure measurement, the first and second fuel pressure measurement corresponding to a high pressure region and a low pressure region, respectively, determining, by the controller, a pressure differential based on the difference between the second fuel pressure measurement and the first fuel pressure measurement, calculating, by the controller, a specific gravity value based in part on the determined pressure differential; and determining, by the controller, if the calculated specific gravity value exceeds a predefined threshold.

In an embodiment a direct injection system is provided, with the direct injection system including a fuel pump fluidly coupled to a fuel supply, a fuel return line, a fuel rail having an inlet fluidly coupled to the fuel pump and an outlet fluidly coupled to the fuel return line, the fuel rail being configured to provide a first portion of fuel to a plurality of fuel injectors, and provide a second portion of fuel to the fuel return line, an orifice disposed within the fuel return line and configured to pass fuel and introduce a measurable pressure difference such that a first pressure is provided before fuel passes through the orifice and a second pressure is provided downstream of the orifice, a first pressure sensor configured to measure the first pressure, a second pressure sensor configured to measure the second pressure, circuitry electrically coupled to the first and second pressure sensors and configured to determine a pressure differential based on a difference between the second measured pressure and the first measured pressure, and calculate a specific gravity value for the second portion of fuel based in part on the determined pressure differential.

In an embodiment, a non-transitory computer-readable medium is provided, the non-transitory computer-readable medium having a plurality of instructions that when executed by at least one processor causing a process to be carried out, the process being configured to receive a first and second fuel pressure measurement, the first and second fuel pressure measurement corresponding to a high pressure region and a low pressure region, respectively, introduced by an orifice within a fuel return line of an engine, determine a pressure differential based on a difference between the second fuel pressure measurement and the first fuel pressure measurement, and calculate a specific gravity value for a fuel of the engine based in part on the determined pressure differential.

These and other features of the present embodiments will be understood better by reading the following detailed description, taken together with the figures herein described. The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION

As a result of the rising price of oil and the growing concern over $CO_2$ emissions, fuel economy has become an increasing concern within the automobile industry. In the U.S. market, for example, the newly implemented standards and regulations such as the Corporate Average Fuel Economy (CAFE) standards put focus on improving fuel consumption in light-duty vehicles. To meet target fuel efficiencies and emissions standards, OEMs (original equipment manufacturers) and engine suppliers have increasingly adopted an approach that includes downsizing and boosting engines. This approach reduces engine displacement while increasing the specific power output by turbocharging in order to maintain torque and power output similar to that of a larger engine. Unfortunately, and as discussed above, downsized and boosted engines may also experience destructive abnormal combustion events such as low-speed pre-ignition, or LSPI. Multiple approaches have been developed to reduce the potential for LSPI, such as using oil/lube additives, engine mapping and fuel injection timing schemes, and mechanical changes. However, at present no single solution eliminates all potential incidences of LSPI, nor allows for real-time engine measurements to accurately identify when an engine is experiencing conditions likely to cause LSPI.

Figure 1:
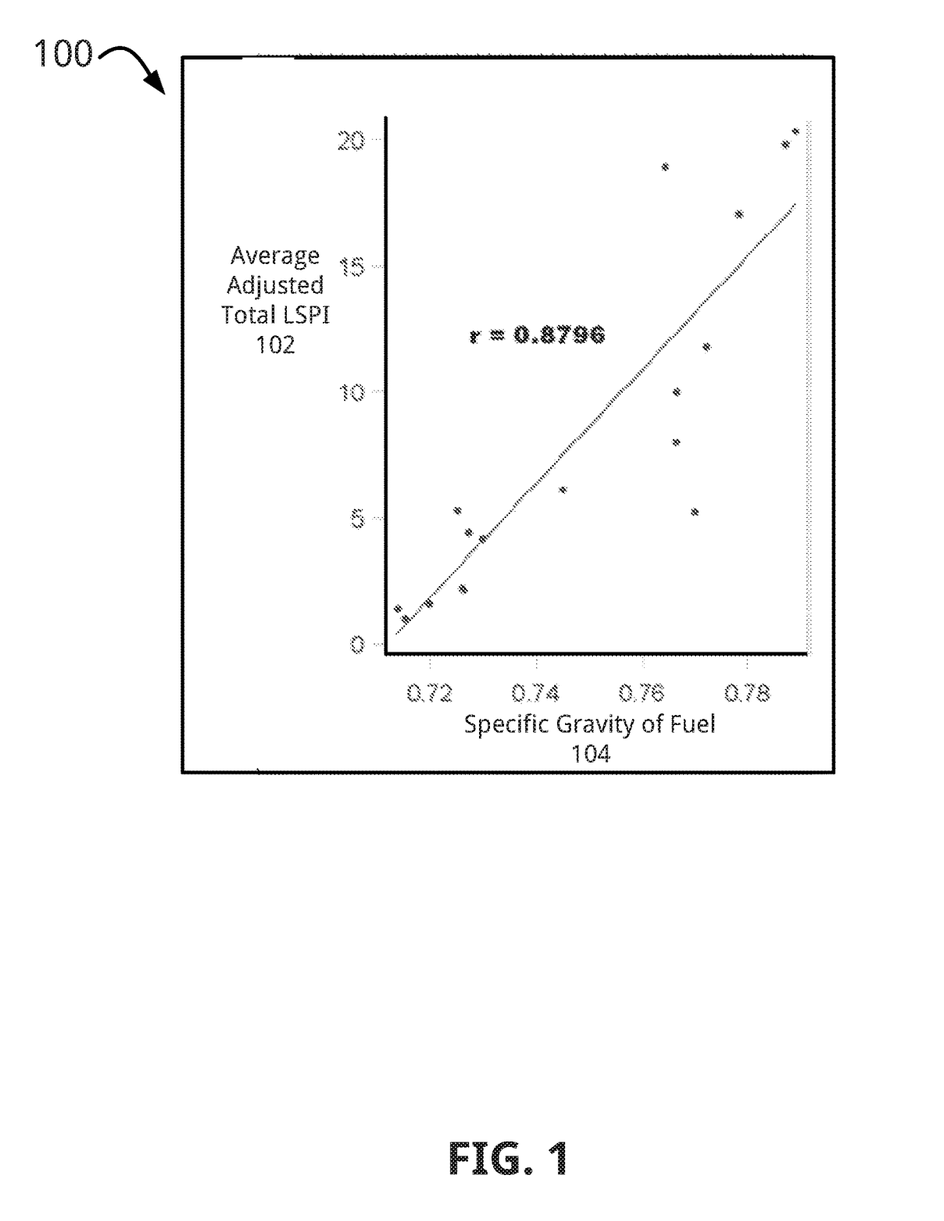
FIG. 1 is graph that illustrates an example set of fuels which suggests a correlation between fuels having a particular specific gravity and the average adjusted total incidences of low-speed pre-ignition within engines using the same, in accordance with an embodiment of the present disclosure.

Aspects and embodiments disclosed herein indicate that a correlation exists between characteristics of combustible fuel and the occurrence of LSPI within engines. For example, and as shown in FIG. 1, a graph 100 illustrates an example set of fuels used within a small-bore engine (e.g., 2.0 L L4) and the resulting number of LSPI incidences for those fuels. As shown, average total incidences of LSPI increased substantially for fuels having a specific gravity (relative to water) at or above a threshold of 0.76. These results therefore identify a correlation which can facilitate additional techniques that minimize or otherwise mitigate incidences of LSPI through online measurements during operation of an engine.

As generally referred to herein, the term "online" refers to measurements performed during operation of the engine. As should be appreciated, the specific gravity of 0.76 is one specific example derived from LSPI testing on a particular set of engines and engine configurations, and is not necessarily a precise threshold for all engine sizes and configurations. However, additional LSPI testing on different desired engine sizes/configurations may yield other specific gravity values, and are also equally applicable to various techniques and methodologies disclosed herein.

Accordingly, techniques are disclosed herein for online measurement of the specific gravity of fuel within an engine, which allow for preventative measures to be executed to minimize or otherwise mitigate the incidence of LSPI when the specific gravity of the fuel exceeds a predefined threshold. In an embodiment, the preventative measures may include, for example, altering or otherwise adjusting an engine map such that an injection timing scheme injects less poor-quality fuel into engine cylinders, thus advantageously preventing the engine from operating at full-power when conditions for LSPI are detected. As should be appreciated, other approaches to mitigating LSPI events are also within the scope of this disclosure. For example, one approach includes dithering the timing of spark occurrences within a combustion chamber to induce a non-destructive knock, with the induced knock consuming deposits within the combustion chamber that may otherwise lead to pre-ignition.

In more detail, a direct injection system is provided herein that allows an engine control unit, or engine controller, to calculate the specific gravity of fuel passing through a fuel rail based on an orifice meter or plate disposed within a fuel return line coupled to an outlet of the fuel rail. The direct injection system may be compatible with any gasoline direct injection (GDI) engine, such as those within light duty vehicles. The direct injection system may also be compatible with diesel engines or any other engine that may burn combustible fuels and potentially experience LSPI. In an embodiment, the direct injection system preferably includes a high-pressure fuel pump coupled to a fuel supply, with the high-pressure fuel pump configured to pressurize fuel up to, for example, about 200 bar for gasoline engines, and up to about 2500 bar for diesel engines. A common fuel rail having a plurality of fuel injectors may include an inlet fluidly coupled to the high-pressure fuel pump, and be configured to receive pressurized fuel and accumulate the same for the purpose of delivering fuel to the fuel injectors at a generally constant flow rate. The common fuel rail may further include an outlet coupled to a fuel return line. The fuel return line may include a solenoid control valve configured to selectively open/actuate based on an electrical control signal provided by the engine control unit. When actuated, the solenoid control valve may allow pressurized fuel to pass into the fuel return line and into a down-stream orifice meter. The down-stream orifice meter may be configured with a diameter $D_1$, with the diameter $D_1$ being less than the diameter $D_2$ of hose/pipe of the fuel return line. Thus, a pressure differential may be introduced such that a first pressure P1 and a second pressure P2 are introduced at a first position upstream of the orifice meter (e.g., proximal to the solenoid control valve) and downstream of the orifice, respectively. The pressure differential values P1 and P2 may be received and utilized by an engine control unit, or engine controller, to calculate a specific gravity for the fuel. As should be appreciated, and in accordance with an embodiment, specific gravity calculations may be based on Bernoulli's equation, wherein density is replaced by specific gravity. In turn, the engine control unit may then compare the calculated specific gravity to a predefined threshold value. In response to the calculated specific gravity exceeding the predefined threshold, the engine control unit may, for example, de-rate the engine by adjusting an engine fuel map. In a general sense, this limits the amount of fuel and air entering into the cylinder at a given speed, thus redefining the torque/lug curve of the engine. In another example, an engine control unit may change the shift points of an automatic transmission to avoid operating at a low RPM when conditions for LSPI are detected. Thus the engine may operate at a higher RPM with a lower BMEP/load, which may impact fuel economy but decrease the potential for engine damage. However, it should be appreciated that numerous other approaches may also be utilized to mitigate instances of LSPI in the event that LSPI conditions are detected. For example, the engine may completely stop operation (e.g., cease all fuel delivery) until suitable/higher-quality fuel is supplied.

Example Direct Injection System and Operation

Various embodiments disclosed herein are directed to a direct injection system configured to calculate a specific gravity of fuel provided to engine cylinders, and adjust engine behavior based on the calculated specific gravity exceeding a predefined threshold in order to minimize or otherwise mitigate conditions giving rise to low-speed pre-ignition (LSPI) events. Although various aspects and scenarios reference a particular category of direct injection systems, namely high-pressure gasoline direct injection (GDI), other fuel injection systems are also within the scope of the disclosure such as diesel engine systems.

Figure 2:
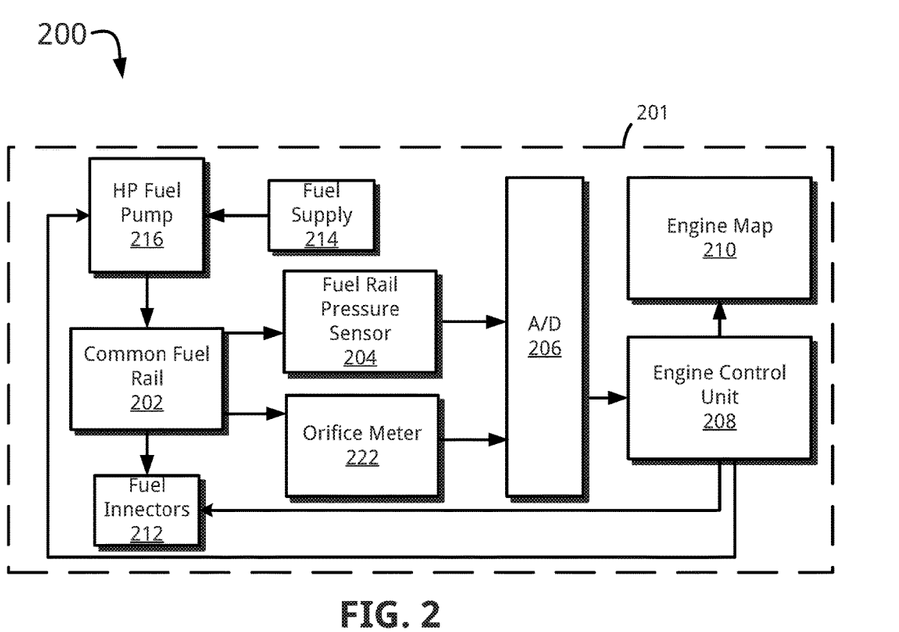
FIG. 2 shows a block diagram of an example direct injection system, in accordance with an embodiment of the present disclosure.

FIG. 2 shows a block diagram illustrating an example direct injection system 200, in accordance with an embodiment of the present disclosure. As shown, the direct injection system 200 includes a common fuel rail 202, a fuel rail pressure sensor 204, electrical signal conditioning circuitry 206, an engine control unit 208, an engine map 210, a plurality of fuel injectors 212, a fuel supply 214, a high-pressure fuel pump 216, and an orifice meter 222 or plate. In an embodiment, the direct injection system 200 is housed within an automobile 201 or other suitable vehicle.

In more detail, the fuel supply 214 may comprise a fuel tank or other suitable container configured to store fuel such as gasoline. The high-pressure fuel pump 216 may comprise any suitable pump capable of pressurizing fuel and providing/displacing the same to the common fuel rail 202. In some cases, the high-pressure fuel pump 216 is a positive displacement pump which allows a known volume of fuel to be displaced per revolution. In other cases, the high-pressure fuel pump 216 may comprise other pumps capable of varying displacement on-the-fly such as, for example, a gear, vane or piston pump. In any such cases, the engine control unit 208 may receive a signal representing the current displacement of the high-pressure fuel pump 216. Alternatively, or in addition to receiving the signal representing the current displacement, the high-pressure fuel pump 216 may receive a signal from, for example, a flow sensor or meter, that measures the current displacement. In any event, the high-pressure fuel pump 216 may be mounted within the fuel tank of the fuel supply 214 (e.g., submerged), or may reside externally at any suitable location within the automobile 201. In some cases, two or more fuel pumps may be present and the single fuel pump illustrated in FIG. 2 should not be construed as limiting. For example, the direct injection system 200 may include a low-pressure transfer pump inside the fuel tank of the fuel supply 214, with the low-pressure transfer pump providing the fuel to the high-pressure fuel pump 216. The high-pressure fuel pump 216 may further include a reservoir configured to store an amount of pressurized fuel. For example, the high-pressure fuel pump 216 may store up to a liter of pressurized fuel, although other reservoir sizes are also within the scope of this disclosure. The high-pressure fuel pump 216 may provide pressurized fuel up to and above 2,500 bars or more.

The common fuel rail 202 may comprise any suitable fuel rail or pipe system configured to provide fuel to the plurality of fuel injectors 212. The common fuel rail 202 is "common" in a sense that each of the plurality of fuel injectors 212 is supplied by the common fuel rail 202, which essentially operates as a pressure accumulator whereby the fuel is stored at a desired pressure prior to being dispersed by the plurality of fuel injectors 212 into associated cylinders. The plurality of fuel injectors 212 may be controlled by the engine control unit 208. For example, the engine control unit 208 may electrically activate the plurality of fuel injectors 212 by a control signal 232 (FIG. 3) which may cause a hydraulic valve that includes a nozzle and plunger within each fuel injector, for example, to mechanically or otherwise hydraulically open, thus causing a precise amount of fuel to be sprayed into associated cylinders.

The fuel rail pressure sensor 204 may be fixedly attached to the common fuel rail 202 and be configured to measure rail pressure. In an embodiment, the fuel rail pressure sensor 204 provides an electrical signal proportional to the measured rail pressure. The fuel rail pressure sensor 204 may be electrically coupled to the electrical signal conditioning circuitry 206, and be configured to provide the electrical signal proportional to the measured rail pressure to the electrical signal conditioning circuitry 206. The electrical signal conditioning circuitry 206 may comprise, for example, analog to digital (A/D) conversion circuitry configured to receive an analog signal and output a digital representation of the same. The electrical signal conditioning circuitry 206 includes an output electrically coupled to the engine control unit. The engine control unit, in turn, may receive a digital representation of the measured rail pressure.

The engine control unit may 208 may comprise, for example, any controller, module or circuitry capable of receiving inputs from various engine components and sensors, and controlling various aspects of engine operation (e.g., using actuators) including the direct injection system 200. The engine control unit 208 may comprise, for example, a microcontroller, a Complex Instruction Set Computer (CISC), a field-programmable gate array (FPGA), Reduced Instruction Set Computer (RISC) processor, x86 instruction set processor, multi-core, microcontroller, an application-specific integrated circuit (ASIC), or central processing unit (CPU). The engine control unit 208 can include storage (not shown) such as non-volatile storage devices including flash memory and/or volatile storage devices such as Random Access Memory (RAM), Dynamic Random Access Memory (DRAM), and Static Ram (SRAM). The engine control unit 208 may include or otherwise receive instructions that when executed cause one or more processes to be carried out, such as the method 600 described below with respect to FIGS. 6A-6B. In any event, the processes variously disclosed herein may be implemented, for example, using software (e.g., C or C++ executing on the controller/processor), hardware (e.g., hardcoded gate level logic or purpose-built silicon) or firmware (e.g., embedded routines executing on a microcontroller), or any combination thereof.

In an embodiment, the engine control unit 208 may comprise a programmable engine control unit. In this embodiment, the programmable engine control unit may be user-configurable and may allow for fine-tuned control over the amount of fuel to be injected into each cylinder during operation of the engine.

The engine map 210 may be stored in a memory (not shown) by the engine control unit 208. The engine map 210 may comprise one or more lookup tables that allow the engine control unit 208 to precisely control a desired amount of fuel to be injected by each of the plurality of fuel injectors 212 depending on engine speed and load. For example, one lookup table may provide a range of rotation per minute (RPM) values for the engine on an X axis and a range of load values on a Y axis. Load may also reflect, for example, a particular position of the accelerator pedal or manifold air pressure. In a general sense, the lookup table may operate similar to that of an excel table such that each cell represents an intersection between a specific RPM value and a particular engine load. Each cell may then contain a duration that corresponds to the prescribed amount of time to actuate the fuel injectors. Thus during engine operation, the engine control unit 208 may continuously perform lookups using the real-time measured RPM and engine load to determine a particular duration of time (e.g., in milliseconds) to have fuel injectors 112 inject fuel into the cylinders. Accordingly, the engine control unit 208 may precisely control engine performance by ensuring a predetermined and precise amount of fuel is provided relative to present engine speed and load.

The orifice meter 222 may comprise, for example, any suitable orifice meter or plate with a hole (or aperture) having a diameter less than that of the fuel return line 221. As should be appreciated, the specific diameter of the orifice hole may be chosen based on a diameter that is small enough to generate a measurable pressure drop across the orifice, but suitably large enough so that the high-pressure fuel pump 216 can be consistently actuated to a consistent displacement without over pressuring the direct injection system 200. The orifice meter 222 may be electrically coupled to an input of the engine control unit 208 by way of the electrical signal conditioning circuitry 206.

Figure 3:
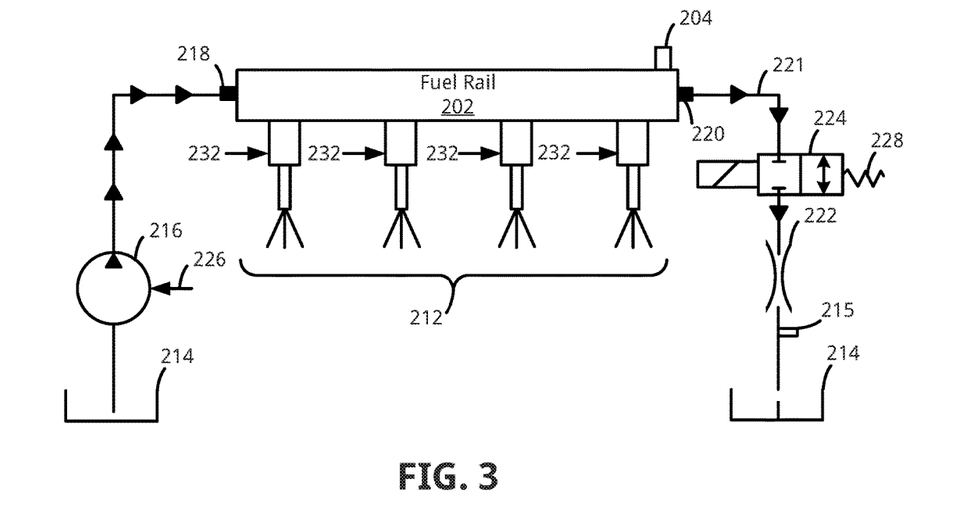
FIG. 3 shows an example embodiment of the direct injection system of FIG. 2 in further detail.

FIG. 3 shows an example embodiment of the direct injection system 200 in further detail. As shown, the high-pressure fuel pump 216 includes an inlet fluidly coupled to the fuel supply 214 and an outlet fluidly coupled to the inlet 218 of the common fuel rail 202. Also as shown, the common fuel rail 202 is fluidly coupled to a plurality of fuel injectors 212, although the disclosure is not necessarily limited to four fuel injectors, as shown. An outlet 220 of the common fuel rail 202 is fluidly coupled to the fuel return line 221 at a first end. A second end of the fuel return line 221 is fluidly coupled to an input of a solenoid control valve 224. An output of the solenoid control valve 224 is fluidly coupled to an inlet of the orifice meter 222. The solenoid control valve 224 may be directly coupled to the orifice meter 222, or coupled to the orifice meter 222 indirectly by a length of hose/pipe provided by the fuel return line 221. In the particular embodiment, an outlet of the orifice meter 222 is fluidly coupled to the fuel supply 214, although in other embodiments the fuel return line 221 does not necessarily directly return fuel to the fuel supply 214. In any event, a fuel return line pressure sensor 215 may be provided to measure down-stream fuel pressure and may be configured to provide a proportional electrical signal of the same to the engine control unit 208.

Figure 7:
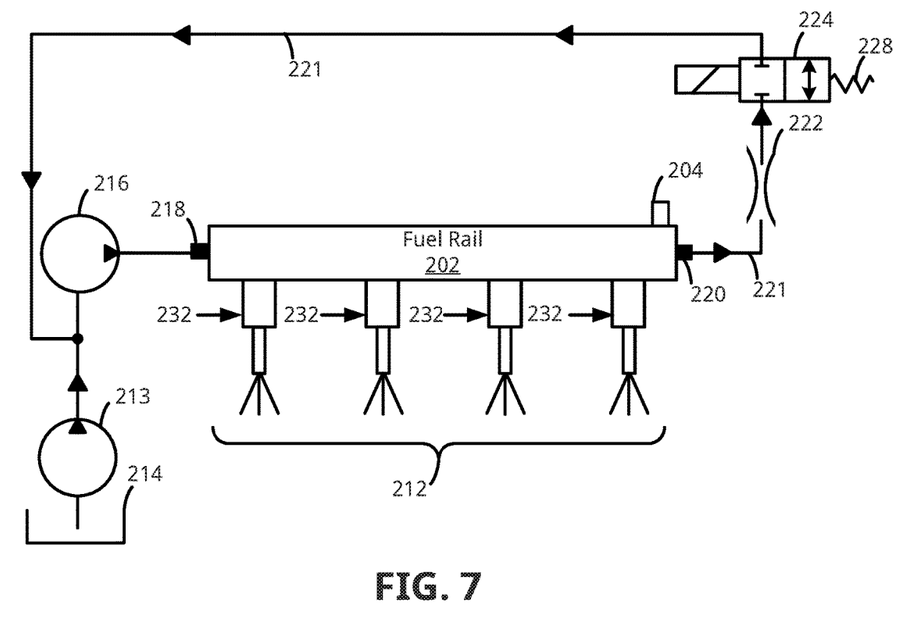
FIG. 7 shows a block diagram of another example direct injection system configured with a low-pressure fuel return line, in accordance with an embodiment of the present disclosure.
Figure 8:
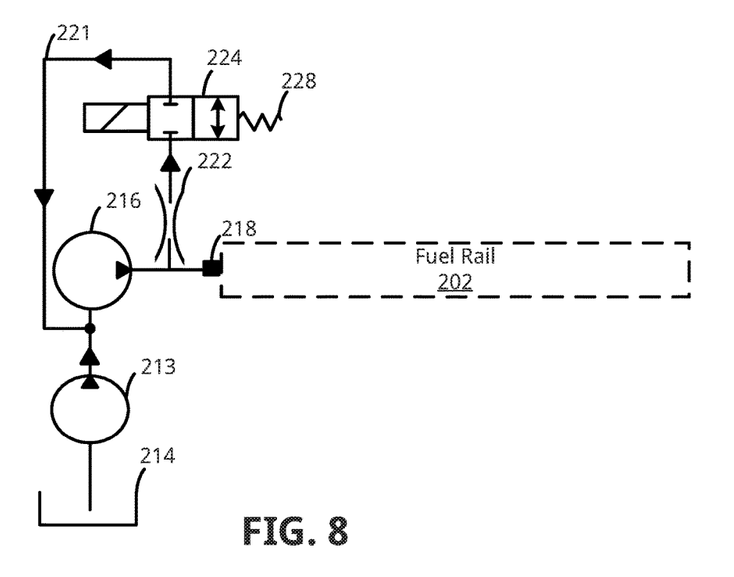
FIG. 8 shows a block diagram of another example direct injection system, in accordance with an embodiment of the present disclosure.

FIG. 7 shows yet another example embodiment of the direct injection system 200 in further detail. The direct injection system 200 may not necessarily return fuel via the fuel return line 221 back to fuel supply 214. For example, and as shown, the direct injection system 200 may include an end of the fuel return line 221 fluidly coupled between an outlet of a low-pressure transfer pump 213 or lift pump and an inlet of the high-pressure fuel pump 216. Thus fuel may be recirculated to the high-pressure fuel pump 216. Alternatively, and as shown in FIG. 8, the fuel return line 221 may include a first end fluidly coupled between an outlet of the high-pressure fuel pump 216 and an inlet 218 of the fuel rail 202, and a second end fluidly coupled between an outlet of the low-pressure transfer pump 213 and the inlet of the high-pressure fuel pump 216. Thus the direct injection system 200 may have a relatively small footprint within an engine. As should be appreciated, numerous variations and permutations for passing fuel through the orifice meter 222 are within the scope of this disclosure.

During engine operation, the high-pressure fuel pump 216 may receive an electrical signal 226 from the engine control unit 208. The electrical signal 226 may be accurately described as a pump command, and may cause the high-pressure fuel pump 216 to actuate to a fixed fuel displacement. At or around the same time, the engine control unit 208 may also provide an electrical signal 232 to the plurality of fuel injectors 212, which may cause the fuel injectors to inject a precise amount of fuel into associated cylinders (not shown), such as discussed above.

Figure 4:
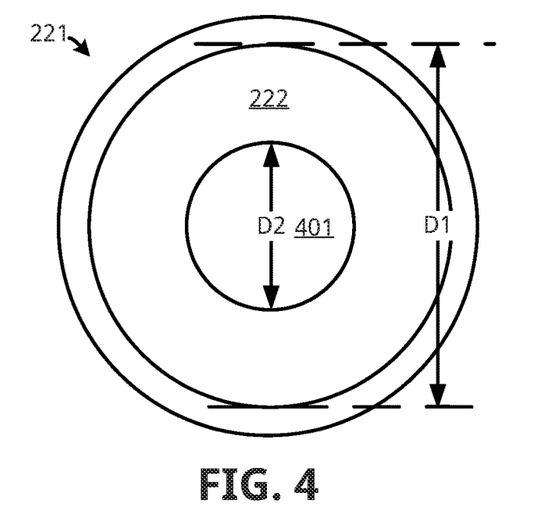
FIG. 4 illustrates a cross-sectional view of an example fuel return line fluidly coupled to the example direct injection system of FIG. 3 and includes an orifice plate disposed therein, in accordance with an embodiment of the present disclosure.
Figure 5:
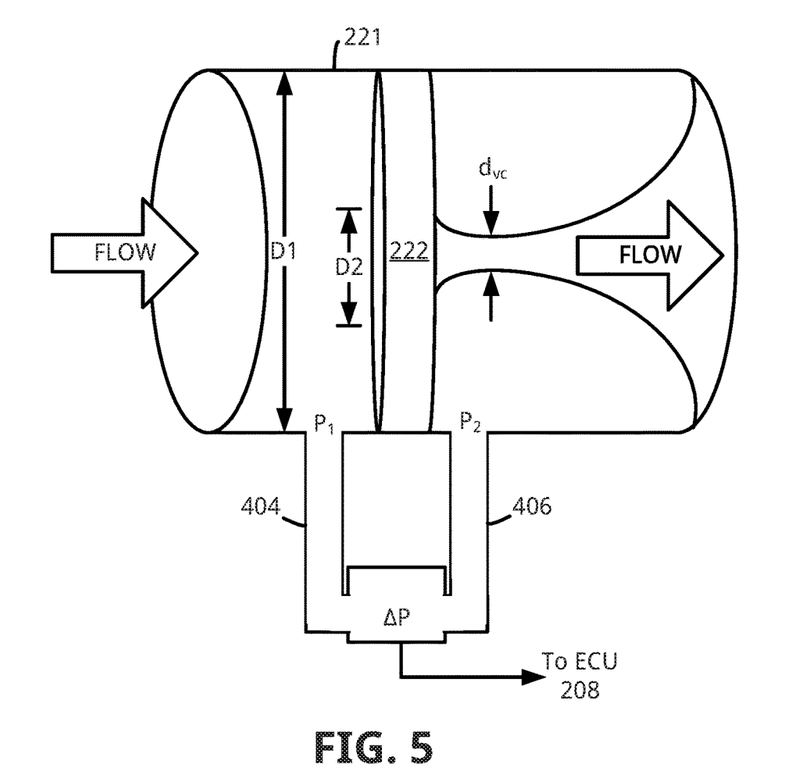
FIG. 5 illustrates a schematic view of the orifice plate of FIG. 4 and a measurable pressure differential introduced by the same within the example fuel return line, in accordance with an embodiment of the present disclosure.

In an embodiment, the engine control unit 208 provides an electrical signal 228 to the solenoid control valve 224 to cause the same to actuate. As a result, fuel is displaced along the fuel return line 221, which encounters the orifice meter 222. For example, and as shown in the example cross-sectional view of the fuel return line 221 of FIG. 4, the fuel return line 221 includes a hose/pipe with a diameter D1. In addition, the fuel return line 221 includes an in-line orifice meter 222, with the orifice meter 222 having an orifice plate that defines a hole 401 or aperture having a diameter D2. To this end, as fuel flows through the fuel return line 221 and the hole 401 of the orifice meter 222, pressure builds up slightly at a region upstream of the orifice meter 222 resulting in pressure $P_1$. As fuel is forced to converge and pass through the orifice meter 222, the velocity increases as the fluid pressure decreases resulting in pressure $P_2$ at a region downstream of the orifice meter 222. Slightly downstream of the orifice the flow reaches its point of maximum convergence, also known as its *vena contracta* ($d_{vc}$), where the velocity reaches its maximum and the pressure reaches its minimum. Beyond that point, the flow expands and the velocity falls resulting in a pressure increase. As should be appreciated, different geometries and configurations of the orifice meter 222 are within the scope of this disclosure and specific embodiment illustrated in FIGS. 4 and 5 are not intended to be limiting.

In accordance with an embodiment, the measurable difference between pressure $P_1$ and $P_2$ allows for calculation of a specific gravity for the fuel passing through the orifice meter 222. As should be appreciated, the flow rate for the fuel is known based on, for example, the engine speed and pump command when the engine is in operation. In some cases, the engine may not be in operation during the calculation, and thus, the flow rate may substantially equal the flow through the high-pressure fuel pump 216. In an embodiment, specific gravity for the fuel may be calculated by reducing Bernoulli's equation, whereby:

$$Q = CA_2 \sqrt{2(P_1 - P_2)/\rho} \qquad \text{Equation (1)}$$

where (Q) is volumetric flowrate at any cross-section (m³/s), (C) is the orifice flow coefficient, ($A_2$) is the cross-sectional area of the hole 401, ($P_1$) is the fluid upstream pressure with dimensions of kg/(m*s²), ($P_2$) is the fluid downstream pressure with dimensions of kg/(m*s²), and ($\rho$) is fluid density (kg/m³). The orifice flow coefficient (C) is defined as:

$$C = \frac{C_d}{\sqrt{1-\beta^4}} \qquad \text{Equation (2)}$$

where $C_d$ being the known coefficient of discharge (dimensionless) and $\beta$ being defined as the ratio of D2 to D1. The coefficient of discharge is the ratio of the actual discharge to the theoretical discharge. Thus solving for ($\rho$):

$$\frac{1}{\rho} = \frac{\left(\frac{Q}{CA_2}\right)^2}{2(P_1 - P_2)} \qquad \text{Equation (3)}$$

where $$\frac{1}{\rho}$$

is the specific density of the fuel relative to water (1.0). Thus the specific gravity of fuel may be calculated and utilized by various aspects and embodiments disclosed herein.

Example Methods and Architecture

In an embodiment, the engine control unit 208 may be configured to execute a method whereby a specific gravity for a fuel passing through the common fuel rail 202 is calculated and used to mitigate engine conditions giving rise to LSPI. One such example method 400 is shown collectively in FIGS. 6A-6B, with additional reference to FIGS. 1 and 3. Note that acts of the method 400 may not necessarily be executed in the particular order shown. Also note that the acts shown in method 400 may not necessarily be executed by the engine control unit 208. For example, hardware such as external control modules/circuits may perform one or more acts of the method 400. Likewise, multiple control modules/circuits may perform all or a portion of the method 400. The method begins in act 602.

Figure 6A:
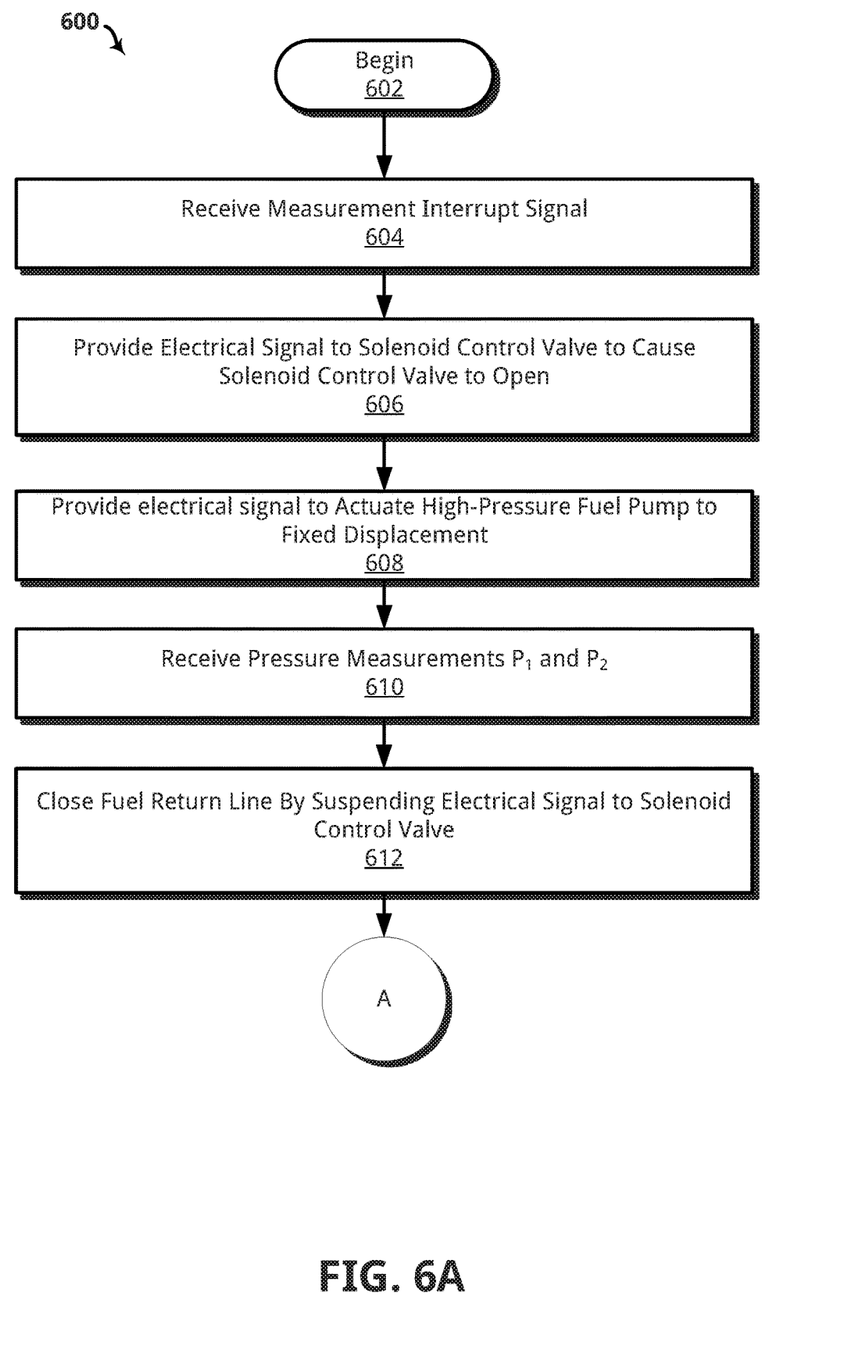
FIGS. 6A-6B collectively illustrate an example method for calculating an online specific gravity value for fuel, and using the same to mitigate conditions giving rise to low-speed pre-ignition events, in accordance with an embodiment of the present disclosure.

In act 604, the engine control unit 208 receives a measurement interrupt signal when, for example, the engine control unit 208 or an associated control module determines de-acceleration of an engine is occurring. In other embodiments, the measurement interrupt signal occurs at any point during operation of the engine and not necessarily exclusively during de-accelerations. In act 606, the engine control unit 208 provides an electrical signal to the solenoid control valve 224 to cause the solenoid control valve to open (e.g., actuate). In act 608, the engine control unit 208 provides an electrical signal to the high-pressure fuel to actuate the same and cause a fixed displacement of fuel into the common fuel rail 202.

In act 610, the engine control until 208 receives pressure measurements $P_1$ and $P_2$. In an embodiment, the pressure value $P_1$ is provided by the rail pressure sensor 204. In other embodiments, the pressure value $P_1$ is provided by a pressure sensor provided by the orifice meter 222. On the other hand, and in accordance with an embodiment, the pressure value P2 may be provided by the downstream fuel pressure sensor 215. In another embodiment, the orifice meter 222 provides at least one of pressure values $P_1$ and $P_2$ to the engine control unit 208, or a signal representing a difference between the two. In act 612, the engine control unit 208 closes the fuel return line 221 by, for example, suspending the electrical signal to the solenoid control valve or otherwise causing it to close (e.g., de-actuate). In some cases, the fuel return line 221 is closed after a predetermined amount of time, such as 10-15 milliseconds. In other cases, the fuel return line 221 may be closed after the engine control unit 208 receives pressure values $P_1$ and $P_2$.

Figure 6B:
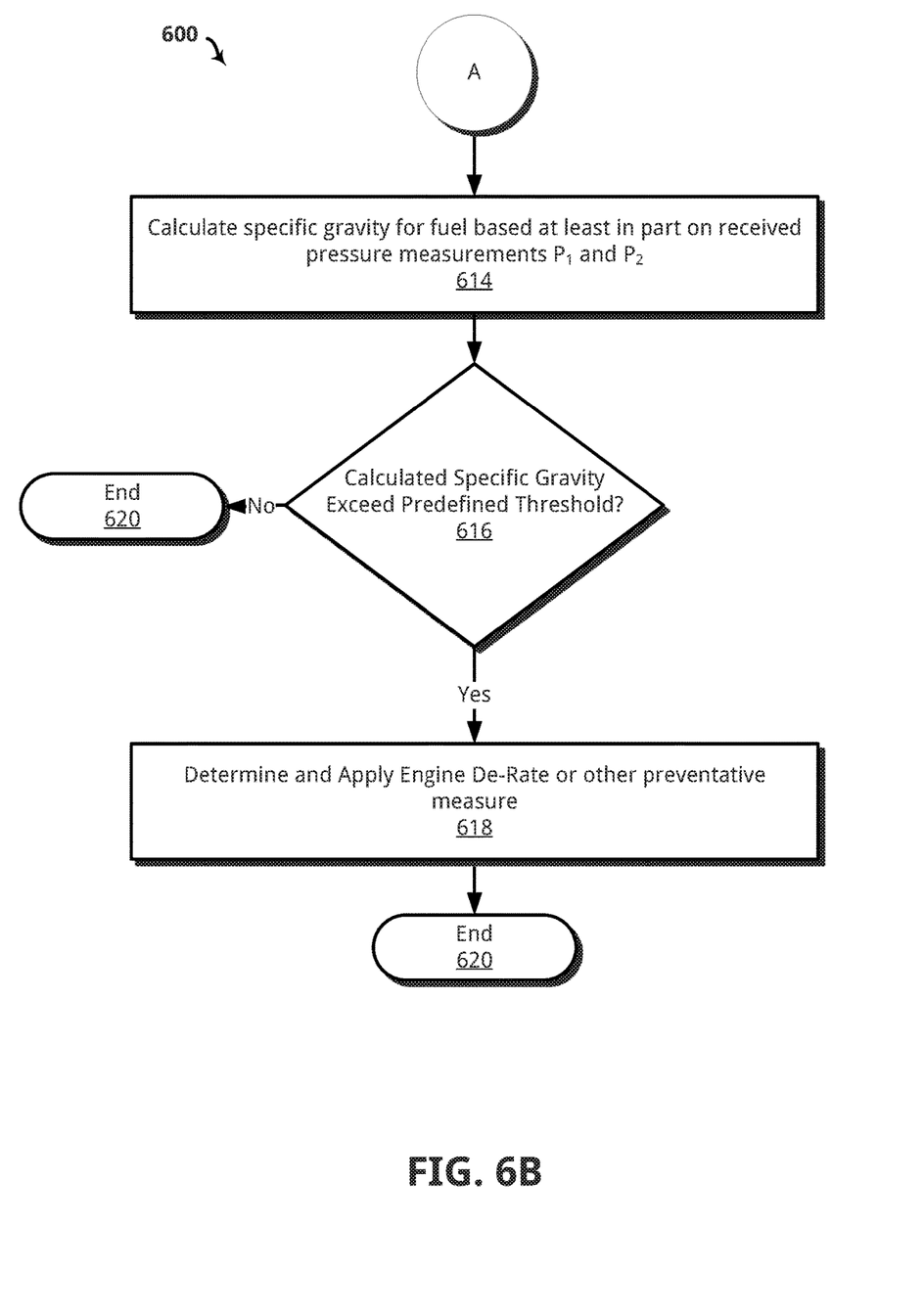

In act 614, the engine control unit 208 calculates a specific gravity for fuel based at least in part on the received pressure measurements $P_1$ and $P_2$. For example, a specific gravity value may be calculated based on Equation (1), and more particularly based on Equation (3) which solves for specific gravity $$\left(\frac{1}{p}\right).$$

The calculation may include, for example, using the known volumetric flow rate (e.g., based on a pump command/known fuel displacement by the high-pressure fuel pump 216), a cross-sectional area of the orifice, diameter D1 of the fuel return line 221, diameter D2 of hole 401, the known orifice flow coefficient, and the pressure measurements $P_1$ and $P_2$.

In act 616, the engine control unit 208 determines if the calculated specific gravity of the fuel exceeds a predefined threshold. In one specific example embodiment, the predefined threshold is about 0.76, although other thresholds may be established based on empirical measurements, heuristic analysis, and other techniques, as should be appreciated. In an embodiment, the predefined threshold is stored in a memory in the engine control unit 208 or is otherwise accessible thereby. In response to the calculated specific gravity being equal to or greater than the predefined threshold, the method 600 continues to act 618. Otherwise, the method 600 ends in act 620.

In act 619, the engine control unit 208 determines and applies a particular engine de-rate or other preventative measure in order to mitigate the conditions that may give rise to LSPI events. In an embodiment, this may include the engine control unit 208 adjusting the engine map 210 such that a fuel injection scheme injects less fuel using the plurality of fuel injectors 212 at least at low speeds (RPMs). For example, the engine control unit 208 may modify entries within the engine map 210 that correspond to low-speed RPMs (e.g., <3000 RPM) while leaving those entries associated with higher RPMs unmodified. In other cases, the engine control unit 208 modifies all entries within the engine map such that a reduction in fuel occurs at all RPMs and load intersections. In still other cases, the engine control unit 208 "swaps" engine maps such that an LSPI-inhibiting engine map is utilized at least during low engine speeds to mitigate the risks of LSPI occurring.

In one embodiment, the engine control unit 208 may also provide an alert to an operator of a vehicle to alert the operator to the engine de-rate, and importantly, a low-quality fuel causing that de-rate. In this embodiment, the engine control unit 208 may provide a visual or audible (e.g., "low-quality fuel detected, engine performance reduced until fuel is replaced.") prompt.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Elements, components, modules, and/or parts thereof that are described and/or otherwise portrayed through the figures to communicate with, be associated with, and/or be based on, something else, may be understood to so communicate, be associated with, and/or be based on in a direct and/or indirect manner, unless otherwise stipulated herein.

Throughout the entirety of the present disclosure, use of the articles "a" and/or "an" and/or "the" to modify a noun may be understood to be used for convenience and to include one, or more than one, of the modified noun, unless otherwise specifically stated. The terms "comprising", "including" and "having" are intended to be inclusive and mean that there may be additional elements other than the listed elements. As used herein, use of the term "nominal" or "nominally" when referring to an amount means a designated or theoretical amount that may vary from the actual amount.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

What is claimed is:

1. A method for determining conditions giving rise to low-speed pre-ignition events in an engine, the method comprising:
   receiving, by a controller, a first and second fuel pressure measurement, the first and second fuel pressure measurement corresponding to a high pressure region and a low pressure region, respectively;
   determining, by the controller, a pressure differential based on the difference between the second fuel pressure measurement and the first fuel pressure measurement;
   calculating, by the controller, a specific gravity value based in part on the determined pressure differential; and
   detecting, by the controller, a condition giving rise to low-speed pre-ignition events in response to the calculated specific gravity value exceeding a predefined threshold.

2. The method of claim 1, wherein the high pressure region and the low pressure region are within a fuel return line, and wherein a first end of the fuel return line is fluidly coupled to an outlet of a fuel rail, and wherein a second end of the fuel return line is fluidly coupled to a solenoid control valve, and wherein the method further comprises:
   actuating the solenoid control valve to pass fuel through an orifice for measurement purposes.

3. The method of claim 2, wherein actuating the solenoid control valve is in response to the controller receiving a measurement interrupt signal.

4. The method of claim 3, wherein the measurement interrupt signal is generated based on detecting de-acceleration of the engine.

5. The method of claim 2, wherein the specific gravity for the fuel is calculated based at least in part on the following equation:

$$\frac{1}{p} = \frac{\left(\frac{Q}{CA_2}\right)^2}{2(P_1 - P_2)}$$

wherein (Q) is volumetric flowrate at any cross-section (m³/s) of the fuel return line, (C) is a orifice flow coefficient of the orifice, (A₂) is a cross-sectional area of a hole of the orifice, (P₁) is the first fuel pressure measurement, (P₂) is the second fuel pressure measurement, and $$\left(\frac{1}{p}\right)$$

is the specific gravity of the fuel.

6. The method of claim 1, the method further comprising:
de-rating the engine in response to the calculated specific gravity value exceeding a predefined threshold, wherein de-rating the engine includes adjusting an engine map, and wherein the adjusted engine map causes a fuel injection scheme implemented by the engine to inject relatively less fuel into cylinders at least during engine speeds under 3000 rotations per minute than when using an unmodified engine map.

7. A direct injection system comprising:
a fuel pump fluidly coupled to a fuel supply;
a fuel return line;
a fuel rail having an inlet fluidly coupled to the fuel pump and an outlet fluidly coupled to the fuel return line, the fuel rail being configured to provide a first portion of fuel to a plurality of fuel injectors, and provide a second portion of fuel to the fuel return line;
an orifice disposed within the fuel return line and configured to pass fuel and introduce a measurable pressure difference such that a first pressure is provided before fuel passes through the orifice and a second pressure is provided downstream of the orifice;
a first pressure sensor configured to measure the first pressure;
a second pressure sensor configured to measure the second pressure;
circuitry electrically coupled to the first and second pressure sensors and configured to:
determine a pressure differential based on a difference between the second measured pressure and the first measured pressure;
calculate a specific gravity value for the second portion of fuel based in part on the determined pressure differential; and
detecting a condition giving rise to low-speed pre-ignition events in response to the specific gravity value exceeding a predefined threshold.

8. The direct injection system of claim 7, wherein the circuitry is further configured to de-rate an engine in response to detecting the condition giving rise to low-speed preignition events.

9. The direct injection system of claim 7, wherein the predefined threshold equals about 0.76.

10. The direct injection system of claim 8, wherein the circuitry de-rates an engine at least in part by causing an engine map to be adjusted, wherein the adjusted engine map causes a fuel injection scheme implemented by an engine control unit to inject relatively less fuel into cylinders at least during engine speeds under 3000 rotations per minute than when using an unmodified engine map.

11. The direct injection system of claim 7, further comprising a solenoid control valve disposed along the fuel return line prior to the orifice and configured to inhibit flow of fuel when de-actuated and allow flow of fuel when actuated, and wherein the circuitry is further configured to:
actuate, in response to receiving a measurement interrupt signal, the solenoid control valve by providing an electrical signal to the solenoid control valve.

12. The direct injection system of claim 11, wherein the measurement interrupt signal is generated as a result of an engine control unit detecting engine de-acceleration.

13. The direct injection system of claim 7, wherein the fuel return line is fluidly coupled to the fuel supply such that fuel passing through the orifice is returned to the fuel supply.

14. The direct injection system of claim 7, wherein the first pressure sensor is a fuel rail pressure sensor fixedly attached to the fuel rail.

15. The direct injection system of claim 7, wherein the specific gravity for the fuel is calculated based at least in part on the following equation:

$$\frac{1}{p} = \frac{\left(\frac{Q}{CA_2}\right)^2}{2(P_1 - P_2)}$$

wherein (Q) is volumetric flowrate at any cross-section (m³/s) of the fuel return line, (C) is a orifice flow coefficient, (A₂) is a cross-sectional area of a hole of the orifice, (P₁) is the first pressure measurement, (P₂) is the second pressure measurement, and $$\left(\frac{1}{p}\right)$$

is the specific gravity of the fuel.

16. The direct injection system of claim 7, wherein the fuel pump is a high-pressure fuel pump configured to pressurize fuel up to 2,000 bars or more.

17. The direct injection system of claim 7, wherein the circuitry is integrated into an engine control unit or an engine control module.

18. A non-transitory computer-readable medium having a plurality of instructions that when executed by at least one processor causing a process to be carried out, the process being configured to:
receive a first and second fuel pressure measurement, the first and second fuel pressure measurement corresponding to a high pressure region and a low pressure region, respectively, introduced by an orifice within a fuel return line of an engine;
determine a pressure differential based on a difference between the second fuel pressure measurement and the first fuel pressure measurement;
calculate a specific gravity value for a fuel of the engine based in part on the determined pressure differential; and
detect a condition giving rise to low-speed pre-ignition events in response to the specific gravity value exceeding a predefined threshold.

19. The computer-readable medium of claim 18, wherein the specific gravity for the fuel is calculated based at least in part on the following equation:

$$\frac{1}{p} = \frac{\left(\frac{Q}{CA_2}\right)^2}{2(P_1 - P_2)}$$

wherein (Q) is volumetric flowrate at any cross-section (m³/s) of the fuel return line, (C) is a orifice flow coefficient of the orifice, ($A_2$) is a cross-sectional area of a hole of the orifice, ($P_1$) is the first fuel pressure measurement, ($P_2$) is the second fuel pressure measurement, and $$\left(\frac{1}{p}\right)$$

is the specific gravity of the fuel.

20. The computer-readable medium of claim 18, wherein the process is further configured to de-rate an engine in response to detecting the condition giving rise to low-speed pre-ignition events.

21. The computer-readable medium of claim 18, wherein the predefined threshold is about 0.76.

22. The computer-readable medium of claim 20, wherein de-rating the engine further includes adjusting an engine map, and wherein the adjusted engine map causes a fuel injection scheme implemented by the engine to inject relatively less fuel into cylinders at least during engine speeds under 3000 rotations per minute than when using an unmodified engine map.

* * * * *